United States Patent
Bischoff et al.

(10) Patent No.: US 10,426,662 B2
(45) Date of Patent: *Oct. 1, 2019

(54) LASER INSTRUMENT FOR EYE THERAPY

(71) Applicant: Carl Zeiss Meditec AG, Jena (DE)

(72) Inventors: Mark Bischoff, Jena (DE); Gregor Stobrawa, Jena (DE); Evangelos Papastathopoulous, Ludwigsburg (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/847,268

(22) Filed: Dec. 19, 2017

(65) Prior Publication Data

US 2018/0168859 A1    Jun. 21, 2018

Related U.S. Application Data

(63) Continuation of application No. 14/113,157, filed as application No. PCT/EP2012/055277 on Mar. 26, 2012, now Pat. No. 9,849,031.

(Continued)

(30) Foreign Application Priority Data

May 12, 2011 (DE) .......................... 10 2011 075 734
Oct. 17, 2011 (DE) .......................... 10 2011 116 369

(51) Int. Cl.
A61B 18/20 (2006.01)
A61F 9/008 (2006.01)

(52) U.S. Cl.
CPC ............ *A61F 9/008* (2013.01); *A61B 18/201* (2013.01); *A61F 9/0084* (2013.01);
(Continued)

(58) Field of Classification Search
CPC .. A61F 9/008; A61F 9/00802; A61F 9/00804; A61F 9/00825; A61F 9/00827;
(Continued)

(56) References Cited

U.S. PATENT DOCUMENTS 4,665,913 A * 5/1987 L'Esperance, Jr. .......................... A61F 9/00804 606/3
4,901,718 A * 2/1990 Bille ....................... A61B 18/20 606/18

(Continued)

FOREIGN PATENT DOCUMENTS

DE  26 11 933 A1  9/1977
DE  86 11 912 U1  12/1986
(Continued)

OTHER PUBLICATIONS

International Search Report for International Application No. PCT/EP2012/055277, filed Mar. 26, 2012, dated Jul. 26, 2012.
(Continued)

*Primary Examiner* — Ahmed M Farah
(74) *Attorney, Agent, or Firm* — Patterson Thuente Pedersen, P.A.

(57) ABSTRACT

A laser instrument for therapy on the human eye, designed for surgery of the cornea, the sclera, the vitreous body or the crystalline lens, especially suitable for use in immediate succession with other instruments for eye diagnosis or eye therapy, in such a way that during the alternating use of the various instruments, the eye or at least the patient preferably remains in a predetermined position and alignment within one and the same treatment area.

16 Claims, 3 Drawing Sheets

Related U.S. Application Data

(60) Provisional application No. 61/485,371, filed on May 12, 2011.

(52) U.S. Cl.
CPC ............... *A61F 2009/0087* (2013.01); *A61F 2009/00865* (2013.01); *A61F 2009/00872* (2013.01); *A61F 2009/00874* (2013.01); *A61F 2009/00887* (2013.01); *A61F 2009/00889* (2013.01)

(58) Field of Classification Search
CPC .. A61F 2009/00861; A61F 2009/00863; A61F 2009/00865; A61F 2009/0087; A61F 2009/00872; A61F 2009/00878; A61F 2009/00885; A61F 2009/00887; A61B 18/20; A61B 2018/2005; A61B 2018/2015
USPC .......................... 606/4–6, 13, 17; 607/88–91
See application file for complete search history.

(56) References Cited

U.S. PATENT DOCUMENTS

| | | | |
|---|---|---|---|
| 5,474,449 A | 12/1995 | Loge et al. | |
| 6,251,113 B1* | 6/2001 | Appelbaum | A61B 17/00 604/22 |
| 6,494,878 B1* | 12/2002 | Pawlowski | A61F 9/008 606/4 |
| 8,920,408 B2* | 12/2014 | Rathjen | A61F 9/00827 606/5 |
| 9,849,031 B2* | 12/2017 | Bischoff | A61B 18/201 |
| 2004/0254568 A1 | 12/2004 | Rathjen | |
| 2009/0182310 A1 | 7/2009 | Gertner et al. | |
| 2010/0094264 A1* | 4/2010 | Rathjen | A61F 9/008 606/4 |
| 2014/0046308 A1 | 2/2014 | Bischoff et al. | |

FOREIGN PATENT DOCUMENTS

| | | |
|---|---|---|
| DE | 94 15 219.5 U1 | 11/1994 |
| DE | 10 2005 001249 A1 | 7/2006 |
| DE | 10 2010 004 696 A1 | 7/2011 |
| EP | 1 486 185 B1 | 9/2006 |
| EP | 1 731 120 A1 | 12/2006 |
| WO | WO 2010/060443 A1 | 6/2010 |
| WO | WO 2012/152496 A1 | 11/2012 |

OTHER PUBLICATIONS

Written Opinion for International Application No. PCT/EP2012/055277, filed Mar. 26, 2012, dated Jul. 26, 2012.
Application and File History for U.S. Appl. No. 14/113,157, filed Oct. 21, 2013. Inventors: Mark Bischoff et al.

* cited by examiner

LASER INSTRUMENT FOR EYE THERAPY

CROSS-REFERENCE TO RELATED APPLICATIONS

The present application is a continuation of application Ser. No. 14/113,157 filed Oct. 21, 2013 entitled "Laser Instrument for Eye Therapy" which is a National Phase entry of PCT Application No. PCT/EP2012/055277, filed Mar. 26, 2012, which claims priority from DE Application No. 10 2011 075 734.1, filed May 12, 2011, claims the benefit of U.S. Provisional Patent Application No. 61/485,371, filed May 12, 2011, and DE Application No. 10 2011 116 369.0, filed Oct. 17, 2011, which applications are incorporated by reference herein in their entirety.

TECHNICAL FIELD

The invention relates to a laser instrument for therapy on the human eye, designed for surgery of the cornea, the sclera, the vitreous body or the crystalline lens, especially suitable for use alternately with other instruments for eye diagnosis or eye therapy, with the eye or at least the patient remaining, during the alternating use of the various instruments, within a treatment area common to all instruments. For intraoperative use in cataract surgery, the laser instrument is, for example, equipped with a femtosecond laser (briefly: fs-laser) and a phacoemulsification instrument.

BACKGROUND

For a correction of ametropia, e.g. by laser surgery of the cornea, a variety of instruments are required, the design of which is appropriate to the respective purpose. At the beginning of such a treatment, instruments are used that are suitable for eye diagnosis, such as, for example, surgical microscopes, optical arrangements for 3D measurement on the cornea, or arrangements for optical coherence tomography. Depending on the result of the diagnosis, therapeutic measures are then settled on and carried out.

Before one can start the actual correction of ametropia by the removal of tissue off the cornea, one must, in the method known as LASIK, first produce a lid on the surface of the cornea that can be folded up and is known as a flap, the thickness of which is substantially less than the thickness of the cornea itself. For this purpose, a "flap-cutting" laser instrument is used, which is known in prior art as a laser keratome or microkeratome. This instrument is used to produce a succession of many photodisruptions of the tissue, each measuring a few micrometers only, which together constitute the flap; this process requires highly precise positioning of the laser beam focus within the cornea in both lateral and axial direction. The treatment laser beam used for this has pulse widths of less than $10^{-12}$ s.

By application of another optical precision instrument and with the flap folded away to expose the internal tissue region, then, tissue is removed off that exposed region to vary the curvature of the cornea until the ametropia is corrected. The removal of tissue is accomplished, e.g., by energy input with a pulsed treatment laser beam. The instruments designed for removing the tissue are known as laser ablation instruments. Alternatively, a method can be employed that is exclusively carried out with a femtosecond laser therapy instrument. Modern methods of lenticular extraction are known by the names of FLEx and SMILE; methods also possible are radial keratotomy (RK) or annular cuts.

The result of the treatment is assessed with a diagnostic instrument, e.g., a 3D measuring instrument, in order to carry out subsequent corrective treatments, if necessary.

All instruments employed have to be positioned relative to the eye according to their respective tasks; they all need to occupy the same working or treatment area surrounding the eye, from which it follows that this area has to be occupied and cleared by each instrument in succession. For an efficient process sequence, the instruments for the successive process steps should be available in the immediate vicinity without, however, obstructing each other by blocking the working or treatment area. Moreover, it should be avoided, if possible, that the patient's eye to be treated has to be re-aligned after each instrument change as required for therapy or diagnosis.

An added requirement is that, at least temporarily, free space for manual operations on the eye must be available; typically, such operations are observed through a surgical microscope. Often, an instrument for ultrasonic phacoemulsification must be kept available in addition, since a complete emulsification of the crystalline lens by application of femtosecond laser is not possible with cataracts of the $2^{nd}$ to $4^{th}$ degrees. In these cases, an ultrasonic phacoemulsification instrument must be employed as a complement to laser treatment, in order to complete the fragmentation of the crystalline lens. Subsequently, the phacoemulsification instrument must be switched to the irrigation/aspiration mode for removing the lens residues and the cortex from the capsule. For these instruments, too, the treatment area has to be cleared, if necessary.

For the efficiency of the treatment process, patient positioning and patient transport are relevant as well. With the refractive surgery described above, what are important apart from maximum position accuracy are comfort as well as aesthetic aspects, whereas the requirements in case of a cataract operation differ in so far as the patients have to be safely positioned in a locally or generally anaesthetized state.

An aspect of particular importance and not to be ignored in the treatment and therapy of the human eye and especially in case of surgical intervention is the sterility of the laser instrument, particularly those objects and parts of the laser instrument that get into contact with the hands of the surgeon and the assistants. Sterilizing the entire laser instrument, though, is extremely difficult and, in fact, impracticable.

SUMMARY

Departing from this, the invention is based on the problem that a laser instrument for therapeutic treatment of the human eye, which is especially suitable for surgery on the cornea or the crystalline lens, should be advanced with regard to sterility and ergonomics so that during complex operations on the eye it is ensured that interaction with other instruments for eye diagnosis or therapy, such as surgical microscopes, phacoemulsification instruments and patient couches of diverse types and makes, is as free as possible of interference and obstruction.

The laser therapy instrument according to the invention has the technical features discussed in terms of the embodiments herein and claimed herein.

An advantage of the invention is that, in an example embodiment, the laser arm supporting the exit lens system for the therapeutic laser beam can, by a swiveling movement, be removed from the working or treatment area far enough so that it is, without restriction, available for the other instruments involved in the treatment.

The swiveling mechanism is, for example, actuated by a motor. By operation of a manually operated control lever or control switch, a fast movement controlled by the user is released, enabling the user to respond immediately in case of any collision.

In addition, an optionally provided force limiting device reduces unwanted hard contact and the risk of bruises. Further, proximity sensors may be provided, by use of which the swiveling speed can be slowed down as the exit lens system approaches the working position at the eye. Conversely, the swiveling speed can be increased if the arm is swiveled out of the treatment area, i.e. away from the eye.

Advantageously, the swiveling movement is carried on until the swiveling arm including the exit lens system for the therapeutic laser beam is, for the most part or even completely, situated within the contour of the instrument body. This is of advantage not only with regard to clearing the treatment area but also with regard to the portability of the instrument, as in this way the sensitive optical components fitted on the laser arm are protected against mechanical damage.

In an example embodiment, positioning the swiveling arm is carried out in two steps, in such a way that
a) the swiveling arm is folded down with an arcuate movement, and
b) the exit optical system vertically approaches the patient's eye by a linear movement.

This linear movement may comprise a parallel movement of the entire swiveling arm, a telescoping extension of the swiveling arm or a combination of these two movements. In this way, a longer reach of the swiveling arm is achieved, without the need for the swiveling arm, in its folded-back state, to have this overall length. Thus, a compact and ergonomically favourable size can be achieved.

Whereas, with a mere swiveling movement of the swiveling arm, it may possibly be necessary to move the surgical microscope out of its normal operating position and subsequently to reposition it, this can be avoided by a vertical approach of the exit optical system to the patient's eye. Repositioning the surgical microscope, i.e. centering, setting the working distance, zooming etc., always entails a prolongation of the total operating time.

It is a particular advantage that the swiveling arm assembly has a height of less than 20 cm, as this corresponds to the normal working distance of the surgical microscope. Preferably, this assembly is provided with an optical interface, so that, during fine adjustment of the swiveling arm and during laser treatment, an overview image of the patient's eye through the surgical microscope is available. This optical interface comprises at least one dichroic mirror, so that observation (with visible light) and laser treatment (with NIR radiation) can work in parallel.

In another example embodiment of the invention, the laser arm can not only be swiveled but also adjusted in all of the three spatial directions X, Y and Z. Control is effected, e.g., by the user with the aid of a joystick or via control software, which for this purpose analyzes an image of the patient, or rather the patient's eye, taken through the exit lens system for the therapeutic laser beam, and homes the laser arm in from the actual position thus determined to a specified required position.

Also of advantage is an example embodiment in which not only the laser arm but also the patient positioning system can be moved for the purpose of eye positioning, if the user so desires.

In order that also a phacoemulsification instrument can be ergonomically and conveniently placed within the user's reach, the laser therapy instrument can be provided with a mechanical coupling device or a special adapter for the phacoemulsification instrument. Advantageously, such an adapter can be provided with means for spatial alignment of the phacoemulsification instrument. Further, structures can be provided for the transmission of electric energy for power supply and/or means for signal transmission between the laser therapy instrument and the coupled phacoemulsification instrument. In this way, the two instruments can jointly use the control and indicating elements. In an example embodiment, the phacoemulsification instrument can be a fully integrated, constituent part of the laser therapy instrument.

Further, the laser therapy instrument can be provided with an interface for the transmission of signals to a local information network or for the reception of signals from such a network. In another example embodiment, there is a direct data link to a surgical microscope, again with the possibility of joint use of control and indicating elements.

And further, the laser therapy instrument can be provided with a trolley running on wheels or rollers to facilitate its conveyance to the site of treatment. As, on the site of its use, the laser therapy instrument has to be positioned in a highly stable and low-vibration manner and in correct vertical alignment, a motor-driven position stabilization facility may be provided. In the simplest case, this consists of vertically extensible props on the bottom side, which lift the instrument off its wheels so as to relieve the wheels and immobilize the instrument, and may simultaneously perform an inclination correction if necessary. Advantageously, this mechanism is coupled to the control of the laser arm swiveling movement in such a way that, in the transport configuration, swiveling the laser arm for medical use is not possible. To ascertain the inclination information needed for inclination correction, a measurement system with a downstream analysis and control system is provided.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
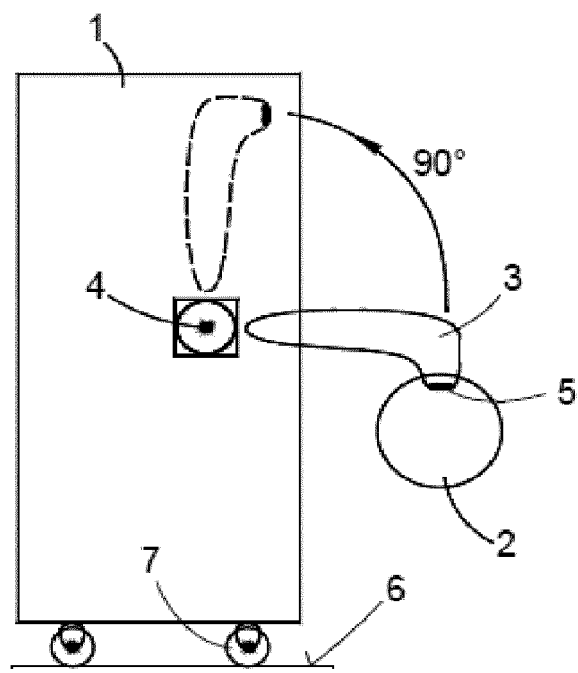
FIG. 1 depicts an embodiment of the invented laser therapy instrument in a view in which various swiveling positions of the laser arm can be seen.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

FIG. 1 illustrates an example embodiment of the invented laser therapy instrument 1 in outline. Let the laser therapy instrument 1 be designed, e.g., for surgery of the cornea of the human eye for the purpose of correcting defective vision by tissue ablation. In this context, this instrument must be used together with other medical-optical instruments, such as, e.g., a surgical microscope for the purpose of diagnosis, a microkeratome or flap cutter for opening the cornea before corrective surgery, or a phacoemulsification instrument for surgery of the crystalline lens.

All instruments involved in this operation are employed in succession, and the treatment area 2 depicted in FIG. 1, in which area the patient, or rather the eye to be treated is positioned, must be made available to each of the instruments for the time it is employed.

The laser therapy instrument 1 is provided with optical structures for guiding and focusing the therapeutic laser beam. Of these optical structures, for the sake of clarity, FIG. 1 shows only the laser arm 3, configured as a swiveling arm. Near one of its ends, the laser arm 3 is mounted in such a way that it can be swiveled about a fulcrum 4, whereas at its opposite end the exit lens system 5 for the therapeutic laser beam is arranged.

As shown here, swiveling is possible, e.g., by an angle of 90°. Adjustable stops are provided (not shown on the drawing) to limit the swiveling range.

In FIG. 1, the laser arm 3 is sketched in a first swivel position in solid lines, and in a second swivel position in broken lines. Each of these two swivel positions defines and end position of the swiveling movement. The solid outline shows the position in which the exit lens system 5 on the laser arm 3 is swiveled into the treatment area 2, in such a way that the laser beam is positioned relative to the eye to be treated as appropriate for the operation step to be carried out. This swivel position is maintained for the time interval in which the invented laser therapy instrument is employed for the purpose of laser ablation from the eye or from implants already placed in it.

Once this operation step has been completed, the laser arm 3 including the exit lens system 5 is swiveled out of the treatment area 2, so that the treatment area 2 is cleared and available for the other instruments actively or passively involved in the operation, with no necessity to considerably, or at all, change the position and alignment of the patient or the eye to be treated.

Figure 2:
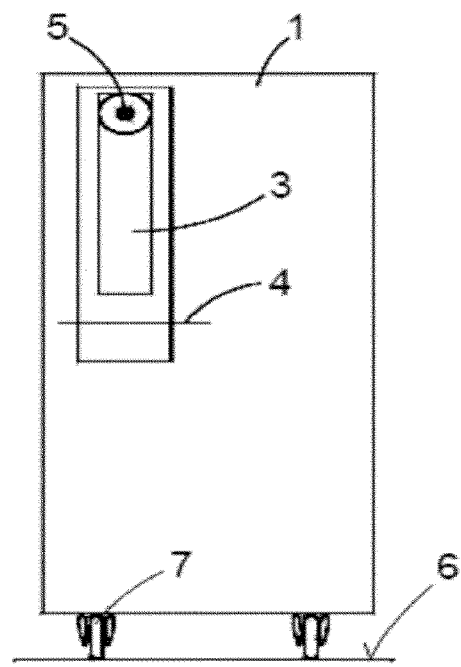
FIG. 2 is a side view of the laser therapy instrument according to FIG. 1, showing the laser arm completely swiveled out of the treatment area and into the housing of the laser therapy instrument.

It is of advantage if the laser arm 3 can be swiveled out of and away from the treatment area 2 to such an extent that the arm, including the exit lens system 5, is situated within the contour of the instrument body, as shown jointly by FIG. 1 and FIG. 2.

Figure 3:
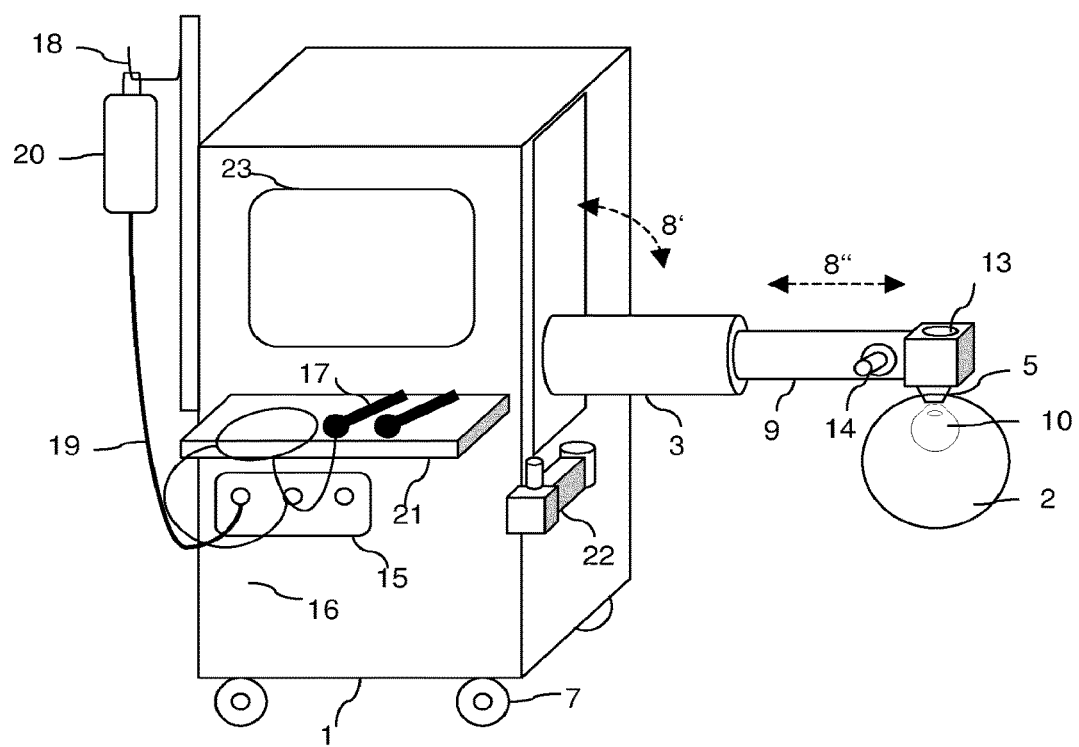
FIG. 3 depicts a second embodiment of the invented laser therapy instrument in a view from which a two-step movement of the laser arm is apparent.

FIG. 3 shows another preferred embodiment of the invented laser therapy instrument 1. In this view, a two-step movement of the laser arm 3 is apparent.

After the laser arm 3 has been folded down with an arcuate movement 8', the exit optical system 5 is vertically approached to the patient's eye 10 in the treatment area 2 with a linear movement 8''.

This telescoping linear movement 8'' may also be implemented as a parallel movement of the entire laser arm 3 or as a combination of these two movements. Here; positioning the laser arm 3 is carried out, e.g., by use of the control lever 13.

After the completion of laser treatment, the laser arm 3 including the exit optical system 5 is moved out of the treatment area 2 by retracting the telescoping extension 9 and folding up 8, so that the treatment area 2 is cleared and available for the other instruments actively or passively involved in the operation, with no necessity to considerably, or at all, change the position and alignment of the patient or the eye to be treated.

Here again it is of advantage if the laser arm 3 can be swiveled out of and away from the treatment area 2 to such an extent that the arm, including the exit lens system 5, is situated within the contour of the instrument body. Thanks to the two-step movement, a longer reach of the laser arm 3 is implemented together with a compact and ergonomically favourable size.

Figure 4:
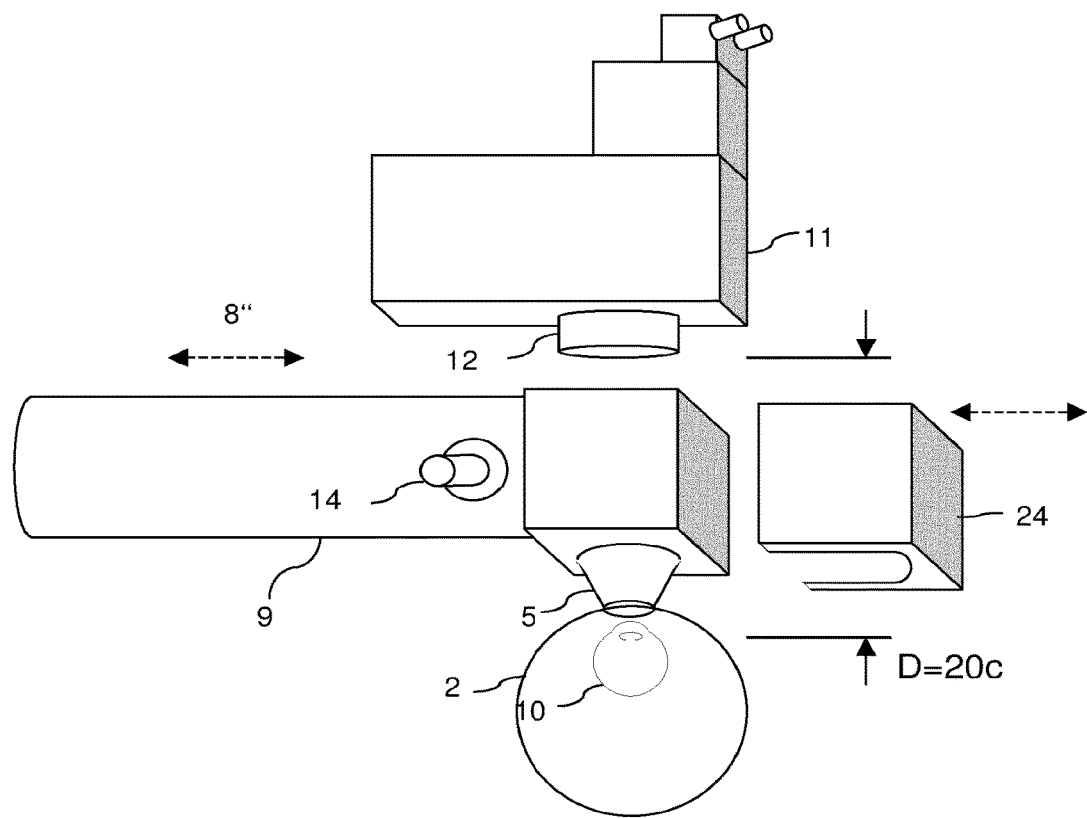
FIG. 4 is a detail view of the extended laser arm with a surgical microscope in accordance with a laser therapy instrument as shown in FIG. 3.

Another example embodiment is shown in FIG. 4, which is a detail view of the laser therapy instrument shown in FIG. 3. The extended laser arm 3 and, in particular, its telescoping extension 9 is situated in the treatment area 2, and the exit optical system 5 has been vertically approached to the eye 10.

A surgical microscope 11 is arranged above the exit optical system 5 in such a way that its objective 12 faces the optical interface (not shown here—see item 13 in FIG. 3), so that, during fine adjustment of the laser arm 3 and during laser treatment, an overview image of the eye 10 is available through the surgical microscope 11.

It is of particular advantage here that the laser arm assembly 3, or at least its telescoping extension 9, has a height D of less than 20 cm, as this corresponds to the normal working distance of the surgical microscope 11.

As FIGS. 1-3 show further, the invented laser therapy instrument 1 is optionally propped up against its support surface 6 by rollers 7, which facilitate its manual conveyance to and from the operating site. In order to put the laser therapy instrument 1 into a stable position and alignment at the operating site despite the rollers 7, a parking brake may be provided (not shown on the drawing), which advantageously is coupled to the swiveling movement of the laser arm so that the laser arm can be swiveled out only after position stabilization at the operating site.

In another example embodiment, an ultrasonic phacoemulsification instrument is integrated into the invented laser therapy instrument. Such an ultrasonic phacoemulsification instrument must be provided anyhow, since a complete emulsification of the crystalline lens by application of femtosecond laser is not possible in case of $2^{nd}$ to $4^{th}$ degree cataracts. In these cases, an ultrasonic phacoemulsification instrument has to be used as a complement to laser treatment, in order to complete the fragmentation of the crystalline lens. Subsequently, the phacoemulsification instrument has to be switched to the irrigation/aspiration mode for removing the lens residues and the cortex from the capsule.

In prior art, the phacoemulsification instrument was positioned at some distance from the patient's head for ergonomic operation by the assistant and for keeping the operating site clear. The instrument's swiveling arm had to be long enough to span the distance between the phacoemulsification instrument and the patient's head, in order to avoid repositioning of the laser system during surgery and the time involved therein.

An aspect in phacoemulsification, i.e. in both irrigation/aspiration and vitrectomy, is the supply of irrigant fluid to the eye to enable efficient removal of lens residues on the one hand and to approximately maintain the pressure conditions in the eye and prevent the capsule from collapsing on the other hand. As a rule, the influx of the liquid is determined passively by the height of the vessel containing the liquid, so that the pressure generated in the eye's anterior chamber increases with the height of the vessel.

In this connection it is of particular advantage if the housing of the invented laser therapy instrument is designed as a kind of rack with various accommodation facilities. This makes it possible to design supplementary equipment such as, e.g., the phacoemulsification instrument as slide-in modules that can be integrated in a simple way.

Accordingly, FIG. 3 shows a preferred embodiment in which the housing of the invented laser therapy instrument is designed as a rack providing accommodation facilities for slide-in modules.

Here, the invented laser therapy instrument 1 is provided with the elements already explained, such as laser arm 3 with telescoping extension 9, exit optical system 5 and control lever 14, which belong to the slide-in module of the laser source.

In addition, the laser therapy instrument 1 features a phacoemulsification instrument 15 designed as a slide-in module, with the handpieces 17 connected via cables 16, accommodation facility 18 for the liquid container, and the liquid container 20 connected to the slide-in module 15 via the hose 19. In addition, a flat tray 21, which may be hinged, is provided for depositing the handpieces 17.

The accommodation facility 18 for the liquid container 20, which may be a bottle or a bag, is provided with a mechanism for height adjustment. Control of the height of the container is either manual or by a motor unit. The control elements required therefore are provided either on the slide-in module itself or as a separate slide-in module and permanently installed in the housing, designed as a rack, of the laser therapy instrument.

Furthermore, the invented laser therapy instrument 1 may be provided with further slide-in modules, e.g., for a control lever 22 or a monitor 23, which may be designed as a touch screen for control. The monitor 23 may show, e.g., the live image of the patient's eye.

The control lever 22 provided for controlling the laser arm 3 preferably features a position changing facility so that it can be actuated from different sides.

As mentioned before, the sterility of the laser therapy instrument and any objects situated nearby is an aspect of special importance in the treatment and therapy of the human eye, particularly in surgical interventions.

If, and especially if, the housing of the invented laser therapy instrument is designed as a rack with accommodation facilities for various slide-in modules, it must be ensured that the laser therapy instrument, even if no slide-in modules are provided, is completely closed in order to be suitable for use in the sterile operating area.

It must be taken into account that all objects that get, or may incidentally get, into contact with the hands of the surgeon and/or the assistant must be sterile, since otherwise there will be an increased risk of a bacterial inflammation of the eye (endophthalmitis), which is the most-feared complication in cataract surgery.

Since, however, sterilization of the entire laser therapy instrument is extremely difficult and, in fact, impracticable, the invented laser therapy instrument is designed in such a way that only parts of the laser therapy instrument are intended to be sterilized by means of an autoclave without essentially impeding the intraoperative use of such an instrument.

For example, the swiveling arm assembly, which is moved to immediately in front of the patient's eye, is provided with a removable hood (item 24 in FIG. 4), which can taken off and sterilized in the autoclave. The control handles on the swiveling arm and on the laser therapy instrument, as well as the tray, are also provided with removable hoods, which can easily be sterilized.

It has proved of advantage if the sterilizable hoods have a colour differing from that of the laser therapy instrument and its elements, as their presence or absence will make it immediately obvious whether sterilization has been carried out and the instrument has been prepared for the next operation.

In conclusion, it should be mentioned that the final approach to the eye, under the appropriate safety conditions, can be performed by raising the patient couch, or lowering the laser therapy instrument, or a movement of the laser arm or only of its exit optical system.

Further development versions of the invented laser therapy instrument are optionally provided with the technical features and details mentioned above under "Description of the Invention" in order to provide the described advantages ensuing from them.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

LIST OF REFERENCE NUMBERS 1 laser therapy instrument
2 treatment area
3 laser arm
4 fulcrum
5 exit lens system
6 support surface
7 rollers
8 folding movement
9 telescoping extension of the laser arm 3
10 patient's eye
11 surgical microscope
12 objective of the surgical microscope 11
13 optical interface
14 control lever
15 phacoemulsification instrument
16 cables
17 handpieces
18 accommodation facility
19 hose
20 liquid container
21 depositing tray
22 control lever
23 monitor
24 removable hood
D working distance of the surgical microscope (approx. 20 cm)

The invention claimed is:

1. A laser therapy instrument:
wherein the laser therapy instrument is structured for surgery on a cornea, a sclera, a vitreous body or a crystalline lines, and is used alternately with other instruments for eye diagnosis or eye therapy, in a common treatment area in which a patient or a patient's eye is positioned, the common treatment area being accessible to the laser therapy instrument and the other instruments in succession;
the laser therapy instrument comprising:
  a beam conducting device including an exit lens system that conducts a therapeutic laser beam to the common treatment area; and
  a device operably coupled to the beam conducting device that moves at least a part of the beam conducting device that includes the exit lens system, into the common treatment area prior to use of the laser therapy instrument and out of the treatment area after the use of the laser therapy instrument, such that the treatment area, after at least the part of the beam conducting device including the exit lens system has been moved out of the treatment area, is freely accessible for using the other instruments;
wherein the beam conducting device that can be moved into and out of the common treatment area comprises a laser arm, wherein the exit lens system included in the laser arm, proceeding from its working position at the eye, is either swiveled out of the treatment area by an angle of approximately 90 degrees along a circular arc path by a swiveling mechanism or moved out of the treatment area along a straight line and a circular arc path;
the swiveling mechanism being actuatable by a motor and being provided with a force limiting device.

2. The laser therapy instrument as claimed in claim 1, in which the swiveling mechanism further comprises proximity sensors.

3. The laser therapy instrument as claimed in claim 2, in which the proximity sensors act to enable slowing the swiveling speed of the exit lens system as the exit lens system approaches the working position at the eye, act to enable increase of the swiveling speed as the laser arm is swiveled out of the treatment area or both of the foregoing.

4. The laser therapy instrument as claimed in claim 1, wherein the laser arm is further movable in a parallel movement of the entire laser arm, a telescoping extension or a combination of the foregoing.

5. The laser therapy instrument as claimed in claim 1, in which the laser arm that can be moved into and out of the common treatment area comprises an optical interface which, during fine adjustment of the laser arm and during laser treatment, enables observation of the patient's eye in a direct view or through a separate optical system.

6. The laser therapy instrument as claimed in claim 1, further comprising a manual or pedal switch that carries out a release of movement, and in which a speed of the movement varies with a distance between the exit lens system and the eye, the movement within a critical distance being slower than outside the critical distance.

7. The laser therapy instrument as claim in claim 1, further comprising strain gauging sensor that are connected to a control unit for movement in such a way that the movement is stopped when strain measured exceeds a specified level.

8. The laser therapy instrument as claimed in claim 1, further comprising a motor drive coupled to a control unit operably coupled to the exit lens system wherein the exit lens system can be positioned in the X, Y and Z spatial directions in addition to movement.

9. The laser therapy instrument as claimed in claim 1, further comprising a motor drive coupled to a control unit operably coupled to the laser arm including the exit lens system wherein the laser arm can be positioned in X, Y and Z spatial directions in addition to movement.

10. The laser therapy instrument as claimed in claim 1, further comprising:
  an imaging system that images the eye to be treated, wherein the exit lens system for the therapeutic laser beam is used as an entrance optical system for imaging light; and
  an image processing system that is connected to the imaging system, and wherein, for the purpose of positioning the exit lens system relative to the eye, the image processing system is connected to control systems for driving the laser arm, with a control system that drives a patient couch or both of the foregoing.

11. The laser therapy instrument as claimed in claim 1, further comprising an information acquisition, information transmission and information processing system for patient-related identification, diagnostic data, therapeutic data, or a combination of the foregoing the system being operably coupled with the other instruments for eye diagnosis or eye therapy.

12. The laser therapy instrument as claimed in claim 1, further comprising:
  rollers, wheels or slide rails operable to change position before and after therapy relative to the other instruments for eye diagnosis or eye therapy, to provide stationary fixation throughout the therapy process, for inclination correction during stationary fixation or a combination of the foregoing.

13. The laser therapy instrument as claimed in claim 12, in which the rollers, wheels or slide rails operable for inclination measurement and/or inclination correction are connected with control systems for the swiveling movement and/or for positioning in the X, Y and Z spatial directions.

14. The laser therapy instrument as claimed in claim 1, further comprising a housing structured as a rack that accommodates various other instruments designed as slide-in modules.

15. The laser therapy instrument as claimed in claim 14, further comprising a phacoemulsification instrument, in which the phacoemulsification instrument comprises a slide-in module including an adjustable height support for a liquid container.

16. The laser therapy instrument as claimed in claim 1, further comprising removable covers that are removable for sterilization.

* * * * *

UNITED STATES PATENT AND TRADEMARK OFFICE
CERTIFICATE OF CORRECTION

PATENT NO.          : 10,426,662 B2
APPLICATION NO.     : 15/847268
DATED               : October 1, 2019
INVENTOR(S)         : Mark Bischoff et al.

Page 1 of 1

It is certified that error appears in the above-identified patent and that said Letters Patent is hereby corrected as shown below:

In the Claims

Column 10, Line 29, delete the first occurrence of "claim" and insert --claimed--

Signed and Sealed this
Fourth Day of February, 2020

Andrei Iancu
*Director of the United States Patent and Trademark Office*